United States Patent [19]

Orban

[11] Patent Number: 4,716,244
[45] Date of Patent: Dec. 29, 1987

[54] PROCESS FOR THE PREPARATION OF STERICALLY HINDERED HYDROXYPHENYLCARBOXYLIC ACID ESTERS

[75] Inventor: Ivan Orban, Basel, Switzerland

[73] Assignee: Ciba-Geigy Corporation, Ardsley, N.Y.

[21] Appl. No.: 853,839

[22] Filed: Apr. 21, 1986

[30] Foreign Application Priority Data

May 2, 1985 [CH] Switzerland .................. 1870/85

[51] Int. Cl.$^4$ ............................................. C07C 67/03
[52] U.S. Cl. .................. 560/75; 203/DIG. 6; 203/33; 203/38; 560/67
[58] Field of Search ............... 560/67, 75; 502/152, 502/224, 343; 203/DIG. 6, 33, 38

[56] References Cited

U.S. PATENT DOCUMENTS

| | | | |
|---|---|---|---|
| 3,330,859 | 7/1967 | Dexter et al. | 560/75 |
| 3,779,945 | 12/1973 | Dexter et al. | 252/404 |
| 4,196,301 | 4/1980 | Spivack et al. | 560/75 |
| 4,536,593 | 8/1985 | Orban et al. | 560/75 |

FOREIGN PATENT DOCUMENTS

1081789  8/1967  United Kingdom .

*Primary Examiner*—Werren B. Lone
*Assistant Examiner*—Vera C. Clarke
*Attorney, Agent, or Firm*—Harry Falber

[57] ABSTRACT

If the transesterification of esters of formula II

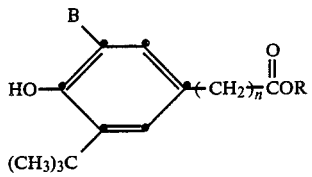

with alcohols of formula III A—(OH)$_m$ is catalysed by treatment with catalytic amounts of an organic or inorganic zinc salt and the resultant melt is subsequently distilled in a short-time distillation apparatus under specific conditions, then compounds of the formula

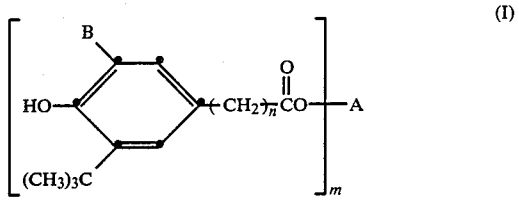

are obtained in virtually quantitative yield, in which formulae I, II and III n is a number from 0 to 2, m is 1 or 2, A is a radical derived from an m-valent aliphatic alcohol, which radical contains 2 to 18 carbon atoms, B is methyl or tert-butyl and R is methyl or ethyl. The products thus obtained contain no troublesome by-products and do not have to be additionally purified.

6 Claims, No Drawings

PROCESS FOR THE PREPARATION OF STERICALLY HINDERED HYDROXYPHENYLCARBOXYLIC ACID ESTERS

The present invention relates to a process for the preparation of sterically hindered hydroxyphenylcarboxylic acid esters, in which process a transesterification reaction is catalysed by treatment with an organic or inorganic zinc salt and the resultant melt is distilled in a short-time distillation apparatus.

Transesterification reactions for the preparation of sterically hindered hydroxyphenylcarboxylic acid esters are known. Thus, for example, German Auslegeschrift No. 1 201 349 and German Offenlegungsschrift No. 1 543 644 describe transesterification reactions of this type in which alkali metal alcoholates are used as catalysts. According to German Offenlegungsschrift No. 2 150 327, transesterification reactions of the same type are catalysed by lithium amide. In all of these processes, varying minor amounts of by-products (usually oxidation products of 2,6-dialkylphenols) are formed. Even very small amounts of such by-products cause a drastic reduction in the storage stability of the desired final product. The unavoidable removal of these by-products involves a great deal of time, labour and energy. In European published application 102 920, in order to solve this problem, it is proposed to catalyse the transesterification by successive treatment with catalytic amounts of an organometallic compound of a metal of the fourth main group or fourth subgroup of the periodic table and an acid earth.

Surprisingly, it has now been found that carrying out the transesterification in the presence of catalytic amounts of an organic or inorganic zinc salt, without solvents and without using acid earths, and subsequently distilling the resultant melt in a short-time distillation apparatus under specific conditions leads to a virtually quantitative yield of pure final product which, since it contains no troublesome by-products, does not have to be additionally purified. A further advantage of this process is that it is carried out without the use of solvents.

Accordingly, the present invention relates to a process for the preparation of compounds of formula I

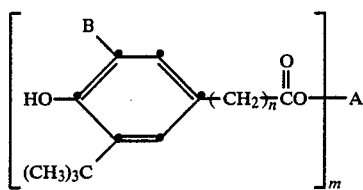

wherein n is a number from 0 to 2, m is 1 or 2, A is a radical derived from an m-valent aliphatic alcohol, which radical contains 2 to 18 carbon atoms, and B is methyl or tert-butyl, by transesterification of about m moles of an ester of formula II

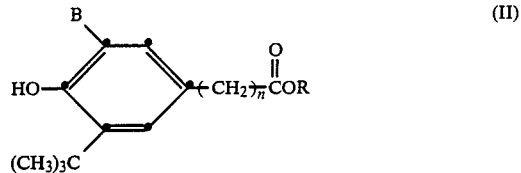

wherein R is methyl or ethyl, with an alcohol of formula III $$A\text{-}(OH)_m \quad (III)$$

which process comprises (a) carrying out the transesterification in the presence of an organic or inorganic zinc salt as catalyst in an amount of 0.05 to 2.0 mol%, based on the ester of formula II, and (b) distilling the resultant melt in a short time distillation apparatus under a pressure in the range from 0.5 to 6 mbar, preferably from 1 to 3 mbar, and at a temperature in the range from 230 to 270° C., preferably from 240 to 260° C., and granulating the melt obtained.

A as a radical derived from an m-valent aliphatic alcohol is an m-valent substituted or unsubstituted aliphatic radical containing 2 to 18 carbon atoms.

If m is 1, then A is straight chain or branched $C_2$-$C_{18}$ alkyl, e.g. ethyl, n-propyl, isopropyl, n-butyl, sec-butyl, tert-butyl, n-pentyl, n-hexyl, 2-ethylhexyl, n-octyl, 1,1,3,3-tetramethylbutyl, n-decyl, n-dodecyl, n-hexadexyl or n-octadecyl, with n-octadecyl being preferred.

If m is 2, then A may be for example $C_2$-$C_{18}$ alkylene, preferably $C_2$-$C_6$ alkylene, such as diemthylene, trimethylene, tetramethylene, hexamethylene, 2,2-dimethyltrimethylene, octamethylens, nonamethylene, decamethylene, dodecamethylyene or octadecamethylene. The alkylene group may be interrupted by —O—, —S— or —N(R)—. Examples of such interrupted alkylene groups are 2-thiaprop-1,3-ylene, 3-thiapent-1,5-ylene, 4-oxaheptamethylene, 3,6-dioxaoctameth-1,8-ylene or 3,6-diazaoctameth-1,8-ylene. If A is interrupted $C_2$-$C_6$ alkylene, it is preferably a $-(CH_2)_2S-(CH_2)_2$ or $-(CH_2)_2O-(CH_2)_2O-(CH_2)_2$ group.

Examples of zinc salts suitable for use as catalysts are zinc chloride, zinc sulfate, zinc stearate and, in particular, zinc acetate, either anhydrous or containing water of crystallisation, e.g. as dihydrate.

The catalyst is preferably employed in an amount of 0.1 to 0.5 mol%, based on the ester of formula II, in the temperature range from 110° to 220° C., most preferably from 140° to 190° C., and under a pressure in the range from 1000 to 2 mbar, most preferably from 250 to 3 mbar, for 2 to 5 hours.

In the case of compounds of formula I wherein m is >1, it is convenient to employ an excess of 1 to 15 mol% of ester of formula II.

Examples of suitable short-time distillation apparatuses are filmtruders, falling film evaporators and, in particular, thin-film evaporators. It is advantageous to carry out the distillation continuously; however, it may also be effected batchwise.

In order to obtain the finished final product in virtually pure, freely flowing, non-dusty form, in which form said product is ready for its specific application, the melt obtained from the short-time distillation only needs to be granulated by conventional methods, e.g. on a cooling conveyor. The process of the present invention is particularly suitable for the preparation of compounds of formula I by transesterification of an ester of formula II with an alcohol of formula III, in which formulae I, II and III n is 2 and m is 1 or 2, A is $C_2$–$C_{18}$ alkyl if m is 1, A is a $-(CH_2)_2O-(CH_2)_2O-(CH_2)_2-$ group if m is 2, and R is methyl.

The preferred process of the present invention is the preparation of octadecyl 3-(3,5-di-tert-butyl-4-hydroxyphenyl)propionate by transesterification of methyl 3-(3,5-di-tert-butyl-4-hydroxyphenyl)propionate with stearyl alcohol, which process comprises (a) carrying out the transesterification in the presence of zinc acetate and (b) distilling the resultant melt in a short-time distillation apparatus under a pressure in the range from 1 to 3 mbar and at a temperature in the range from 240° to 270° C., and granulating the melt obtained.

The esters of formula II, the alcohols of formula III and the catalysts are either known substances or they can be prepared by generally known processes.

The compounds of formula I are valuable stabilisers for organic materials which undergo decomposition, e.g. for synthetic organic polymers, animal and vegetable oils, hydrocarbons, lubricants and the like.

The invention is illustrated by the following non-limitative Examples.

EXAMPLE 1

(a) A flask equipped with a dephlegmator which has been heated to 80° C. is charged with 1051 g (3.6 moles) of methyl 3-(3,5-di-tert-butyl-4-hydroxyphenyl)propionate and 1001 g (3.7 moles) of stearyl alcohol, and the batch is heated to 80° C. Then 1.35 g (0.007 mole) of anhydrous zinc acetate are added. Subsequently, under nitrogen and at normal pressure, the batch is heated to 175° C. During heating, the resultant methanol is distilled off in the condenser. At 175° C., the flask is then evacuated stepwise at 1 to 3 mbar over 1 hour, during which time the methanol distillation is continued.

Finally, the batch is stirred for a further hour at 175° C. and 1 to 3 mbar.

(b) The resultant slightly yellowish melt is continuously passed through a thin-film evaporator (pressure: 1 to 3 mbar; temperature: 240 to 270° C.). The product melt is cooled in the lower part of the evaporator and has a temperature of 60° to 8° C. when it leaves the evaporator. The melt is subsequently poured onto a tray. After the melt has solidified, it is comminuted.

Under operating conditions the melt is granulated direct.

The yield is 1900 g (99.5 % of theory) of octadecyl 3-(3,5-di-tertbutyl-4-hydroxyphenyl)propionate with a melting point of 50° to 51° C.

EXAMPLE 2

The procedure of Example 1 is repeated with the one exception that instead of 1001 g only 972 g (3.6 moles) of stearyl alcohol are employed.

The yield is 1895 g (99.3 % of theory) of octadecyl 3-(3,5-di-tertbutyl-4-hydroxyphenyl)propionate with a melting point of 50° to 51° C.

EXAMPLE 3

The procedure of Example 1 is repeated, except that the transesterification is carried out at 160° C. instead of at 175° C. and the final stirring (at the end of step a) lasts 2 hours instead of 1 hour. The product of Example 1 (with the same melting point) is obtained in the same yield.

EXAMPLE 4

The procedure of Example 1 is repeated, except that 1.6 g (0.007 mole) of zinc acetate dihydrate are used as catalyst and, after the addition of said catalyst, the reaction mixture is first stirred for 15 minutes at 80° C./1–3 mb (removal of the water of hydration) and only then heated at normal pressure to 175° C. The product of Example 1 (with the same melting point) is obtained in the same yield.

What is claimed is:

1. A process for the preparation of a compound of formula I

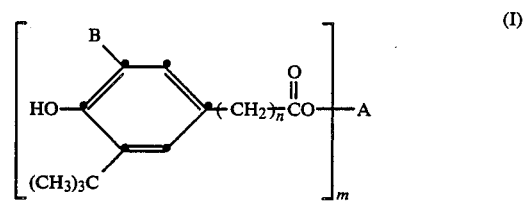

wherein n is a number from 0 to 2, m is 1 or 2, A is a radical derived from an m-valent aliphatic alcohol, which radical contains 2 to 18 carbon atoms, and B is methyl or tert-butyl, by transesterification of about m moles of an ester of formula II at a temperature of 110° to 220° C. and under a pressure of 1000 to 2 mbar,

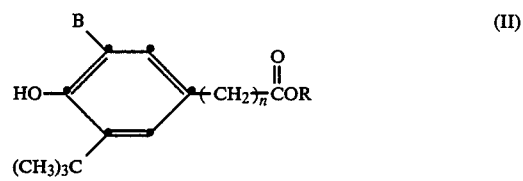

wherein R is methyl or ethyl, with an alcohol of formula III $$A-(OH)_m \qquad (III)$$

which process comprises (a) carrying out the transesterification in the presence of an organic or inorganic zinc salt in an amount of 0.05 to 2.0 mol%, based on the ester of formula II, and (b) distilling the resultant melt in a short-time distillation apparatus under a pressure in the range from 0.5 to 6 mbar and at a temperature in the range from 230° to 270° C., and granulating the melt obtained.

2. A process according to claim 1, wherein the catalyst is zinc acetate.

3. A process according to claim 1 for the preparation of a compound of formula I by esterification of an ester of formula II with an alcohol of formula III. in which formulae I, II and III n is 2 and m is 1 or 2, A is $C_2$–$C_{18}$ alkyl if m is 1, A is a $-(CH_2)_2O-(CH_2)_2O-(CH_2)_2-$ group if m is 2, and R is methyl.

4. A process according to claim 1, which comprises employing the catalyst in the transesterification in an amount of 0.1 to 0.5 mol%, based on the ester of formula II.

5. A process according to claim 1, which comprises carrying out the distillation of the melt in the short-time distillation apparatus under a pressure in the range from 1 to 3 mbar and at a temperature in the range from 240° to 260° C.

6. A process according to claim 1 for the preparation of octadecyl 3-(3,5-di-tert-butyl-4-hydroxyphenyl)propionate by transesterification of methyl 3-(3,5-di-tert-butyl-4-hydroxyphenyl)propionate with stearyl alcohol.

* * * * *